(12) United States Patent
Lange et al.

(10) Patent No.: US 9,995,133 B2
(45) Date of Patent: Jun. 12, 2018

(54) BEND MEASUREMENTS OF ADJUSTABLE MOTOR ASSEMBLIES USING MAGNETOMETERS

(71) Applicant: HALLIBURTON ENERGY SERVICES, INC., Houston, TX (US)

(72) Inventors: Gustav Edward Lange, Millet (CA); Kennedy John Kirkhope, Leduc (CA)

(73) Assignee: Halliburton Energy Services, Inc., Houston, TX (US)

( * ) Notice: Subject to any disclaimer, the term of this patent is extended or adjusted under 35 U.S.C. 154(b) by 87 days.

(21) Appl. No.: 14/917,705

(22) PCT Filed: Dec. 31, 2013

(86) PCT No.: PCT/US2013/078420
§ 371 (c)(1),
(2) Date: Mar. 9, 2016

(87) PCT Pub. No.: WO2015/102599
PCT Pub. Date: Jul. 9, 2015

(65) Prior Publication Data
US 2016/0215610 A1 Jul. 28, 2016

(51) Int. Cl.
*E21B 17/20* (2006.01)
*E21B 47/024* (2006.01)
(Continued)

(52) U.S. Cl.
CPC .............. *E21B 47/024* (2013.01); *E21B 7/06* (2013.01); *E21B 7/067* (2013.01); *E21B 17/20* (2013.01);
(Continued)

(58) Field of Classification Search
CPC .... E21B 17/20; E21B 47/024; E21B 47/0905; E21B 47/12; E21B 7/067; G01N 27/12
See application file for complete search history.

(56) References Cited

U.S. PATENT DOCUMENTS 2,943,397 A 7/1960 Ring et al.
4,303,994 A 12/1981 Tanguy et al.
(Continued)

FOREIGN PATENT DOCUMENTS

WO 0129371 4/2001

OTHER PUBLICATIONS

International Patent Application No. PCT/US2013/078420, International Search Report and Written Opinion, dated Sep. 25, 2014, 18 pages.
(Continued)

*Primary Examiner* — D. Andrews
*Assistant Examiner* — Dany E Akakpo
(74) *Attorney, Agent, or Firm* — Kilpatrick Townsend & Stockton LLP

(57) ABSTRACT

A wellbore assembly is provided that can include a first motor housing assembly member and a second motor housing assembly member that can bend relative to the first motor housing assembly at a bend location. The assembly can also include a magnet positioned to emit a magnetic field. A sensor can be magnetically coupled with the magnet and positioned to detect the strength of the magnetic field emitted by the magnet. Based on the strength of the magnetic field detected by the sensor, the amount of bend or bend direction of the second motor housing assembly member relative to the first motor housing assembly member can be determined.

26 Claims, 8 Drawing Sheets

(51) Int. Cl.
*E21B 47/12* (2012.01)
*E21B 7/06* (2006.01)
*G01N 27/72* (2006.01)
*E21B 47/09* (2012.01)

(52) U.S. Cl.
CPC .......... *E21B 47/0905* (2013.01); *E21B 47/12* (2013.01); *G01N 27/72* (2013.01)

(56) References Cited

U.S. PATENT DOCUMENTS

| | | | |
|---|---|---|---|
| 4,324,297 A | 4/1982 | Denison et al. |
| 4,407,374 A | 10/1983 | Wallussek et al. |
| 4,445,578 A | 5/1984 | Millheim et al. |
| 4,880,066 A | 11/1989 | Steiginga et al. |
| 4,894,923 A | 1/1990 | Cobern et al. |
| 5,117,927 A | 6/1992 | Askew |
| 5,194,859 A | 3/1993 | Warren et al. |
| 5,394,951 A | 3/1995 | Pringle et al. |
| 5,602,541 A | 2/1997 | Wallis et al. |
| 5,646,611 A | 7/1997 | Dailey et al. |
| 6,068,394 A | 5/2000 | Dublin et al. |
| 6,192,748 B1 | 2/2001 | Miller et al. |
| 6,273,189 B1 | 8/2001 | Gissler et al. |
| 6,405,808 B1 | 6/2002 | Lovell et al. |
| 6,585,061 B2 | 7/2003 | Radzinski et al. |
| 6,877,241 B2 | 4/2005 | Barr et al. |
| 7,114,565 B2 | 10/2006 | Estes et al. |
| 7,503,403 B2 | 3/2009 | Jogi et al. |
| 7,506,696 B2 | 3/2009 | Weston et al. |
| 7,556,105 B2 | 7/2009 | Krueger et al. |
| 7,725,263 B2 | 5/2010 | Sugiura et al. |
| 7,870,912 B2 | 1/2011 | Dolgin et al. |
| 7,882,904 B2 | 2/2011 | Von Gynz-Rekowski et al. |
| 8,302,705 B2 | 11/2012 | Downton |
| 8,360,172 B2 | 1/2013 | Santelmann |
| 8,428,879 B2 | 4/2013 | Ekseth et al. |
| 8,434,567 B2 | 5/2013 | Menezes et al. |
| 2003/0094310 A1 | 5/2003 | Eppink et al. |
| 2005/0109097 A1 | 5/2005 | Bogath et al. |
| 2005/0161258 A1 | 7/2005 | Lockerd et al. |
| 2006/0028321 A1* | 2/2006 | Kennedy ............. E21B 47/0905 340/385.1 |
| 2006/0045408 A1 | 3/2006 | Jones et al. |
| 2006/0157278 A1 | 7/2006 | Dolgin et al. |
| 2007/0175639 A1 | 8/2007 | Hoen et al. |
| 2008/0035376 A1* | 2/2008 | Freyer ................... E21B 7/062 175/45 |
| 2009/0260823 A1 | 10/2009 | Prince-Wright et al. |
| 2011/0162891 A1 | 7/2011 | Camp et al. |
| 2011/0284292 A1 | 11/2011 | Gibb et al. |
| 2012/0013339 A1 | 1/2012 | Kuckes |
| 2012/0143521 A1 | 6/2012 | Chen et al. |
| 2012/0205154 A1 | 8/2012 | Lozinsky et al. |
| 2013/0292176 A1 | 11/2013 | Ekseth et al. |
| 2013/0304384 A1 | 11/2013 | Rabinovich et al. |
| 2014/0196953 A1 | 7/2014 | Chitwood et al. |
| 2016/0040525 A1 | 2/2016 | Lange et al. |

OTHER PUBLICATIONS

Canadian Patent Application No. 2,924,358, Office Action, dated Feb. 13, 2017, 3 pages.
U.S. Appl. No. 14/430,068, Non-Final Office Action, dated Apr. 21, 2017, 9 Pages.
U.S. Appl. No. 15/026,702, "Non-Final Office Action", dated Feb. 26, 2018, 13 pages.

* cited by examiner

BEND MEASUREMENTS OF ADJUSTABLE MOTOR ASSEMBLIES USING MAGNETOMETERS

CROSS-REFERENCE TO RELATED APPLICATIONS

This is a U.S. national phase under 35 U.S.C. § 371 of International Patent Application No. PCT/US2013/078420, titled "Bend Measurements of Adjustable Motor Assemblies Using Magnetometers" and filed Dec. 31, 2013, the entirety of which is incorporated herein by reference.

TECHNICAL FIELD

The present disclosure relates generally to devices for use in well systems. More specifically, but not by way of limitation, this disclosure relates to measuring a bend of an adjustable motor assembly using one or more magnetometers.

BACKGROUND

A well system (e.g., oil or gas wells for extracting fluids from a subterranean formation) can include a drill string for forming a wellbore. A drill string can include a bottom hole assembly with a drill bit, stabilizers, a downhole motor, or other components.

A drill string can be used to drill a directional (or deviated) wellbore that is not vertical in its entirety. Directional wellbores can enhance production of the wellbores. To obtain an angle of inclination to drill directional wells, downhole drilling motors can include adjustable housing assemblies. An adjustable housing assembly can allow the drill operator to change the inclination of a housing assembly without replacing the entire bent housing section. An amount of bend downhole of an adjustable housing assembly can be challenging to obtain.

DETAILED DESCRIPTION

Figure 1:
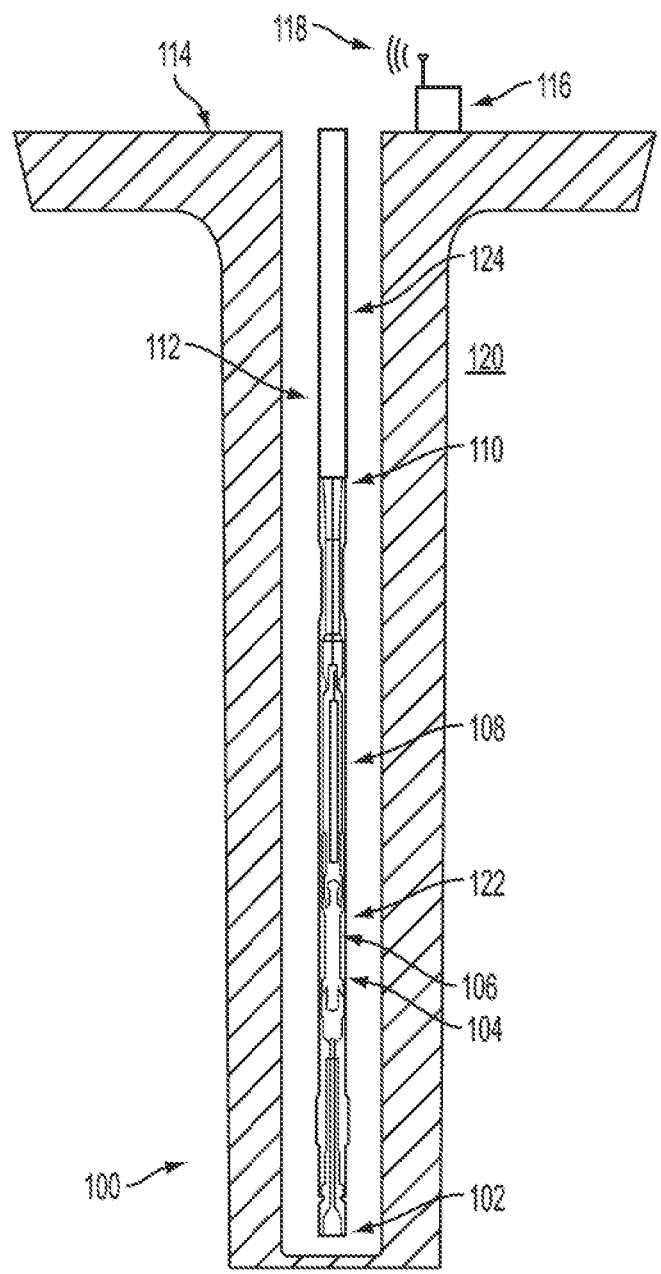
FIG. 1 is a cross-sectional view of one embodiment of a system that includes an adjustable motor assembly for which bend measurements can be determined using magnetometers.

Certain aspects and features of the present disclosure are directed to determining bend measurements of adjustable motor assemblies using magnetometers. The adjustable motor assembly can include a first motor housing assembly member. The adjustable motor assembly can further include a second motor housing assembly member. The second motor housing assembly member can be coupled to the first motor housing assembly member so that the first motor housing assembly member can bend relative to the second motor housing assembly member at a bend location in a wellbore. The adjustable motor assembly can also include a magnet and a sensor. In one embodiment, the magnet can be positioned on the first motor housing assembly member so a sensor can detect the strength of the magnetic field emitted by the magnet. The magnet can be an electromagnet. In such an embodiment, the sensor can be magnetically coupleable with the magnet and positioned on the second motor housing assembly member to detect the strength of the magnetic field emitted by the magnet. The sensor is a magnetometer.

In another embodiment, the adjustable motor assembly can further include a third motor assembly member located inside the first or second motor housing assembly members. The third motor assembly member can be a mandrel. In one such embodiment, a magnet can be positioned on the third motor assembly member so that the sensor can detect the strength of the magnetic field emitted by the magnet. The sensor can be positioned on the first or second motor housing assembly members for detecting the strength of the magnetic field emitted by the magnet. In another embodiment, the magnet can be positioned on the first or second motor housing assembly members. The sensor can be positioned on the third motor assembly member to detect the strength of the magnetic field emitted by the magnet. In some embodiments, the third motor assembly member can rotate around a rotation axis.

The distance between the sensor and the magnet can change as the first motor housing assembly member bends relative to the second motor housing assembly member. The sensor measurement of the strength of the magnetic field emitted by the magnet can change as the distance changes. The changed sensor measurement can be used to determine the amount of bend or bend direction of the first motor assembly housing member relative to the second motor assembly housing member.

In one example, an adjustable motor assembly can be a part of a bottom hole drilling assembly deployed in a wellbore. The first and second motor housing assembly members can be drill motor housing assembly members of the adjustable motor assembly. A drill operator can cause the adjustable motor assembly to bend at a bend location in the wellbore such that a first motor assembly housing member bends relative to a second motor assembly housing member at the bend location. As the first housing member bends relative to the second housing member, the distance between a magnet and a sensor can change. The strength measurements from the sensor can be used to determine the amount of bend and, in some embodiments, the bend direction of the first motor housing member relative to the second motor housing member. Assemblies according to some embodiments can allow the drill operator to confirm that the adjustable motor assembly is functioning properly or predict how the bottom hole assembly will perform in a formation.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

FIG. 1 is a cross-sectional view side of one embodiment of a system 100 that includes an adjustable motor assembly 122 for which bend measurements can be determined using magnetometers. In this example, the system 100 is a well system (e.g., an oil or gas well for extracting fluids from a subterranean formation). The system 100 can include a wellbore 112 drilled out of a formation 120 from a surface 114. A drill string 124, which can contain a bottom hole assembly for drilling, can be located in the wellbore 112. The bottom hole assembly can include an upper connection 110, a power section 108, and a drill bit 102. The power section 108 can include a motor assembly 122 with an adjustable housing 104 that can bend at a bend location 106.

The system 100 can also include a computing device 116 for receiving bend measurements or direction measurements. The computing device 116 can be positioned at the wellbore surface 114, below ground, or offsite. The computing device 116 can include a processor interfaced with other hardware via a bus. A memory, which can include any suitable tangible (and non-transitory) computer-readable medium such as RAM, ROM, EEPROM, or the like, can embody program components that configure operation of the computing device 116. In this example, the computing device 116 can further include input/output interface components and additional storage.

The computing device 116 can receive bend measurements or direction measurements via a communication device 118. The communication device 118 can represent one or more of any components that facilitate a network connection. In this example, the communication device 118 is wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In other embodiments, the communication device 118 can be wired and can include interfaces such as Ethernet, USB, or IEEE 1394.

Figure 2A:
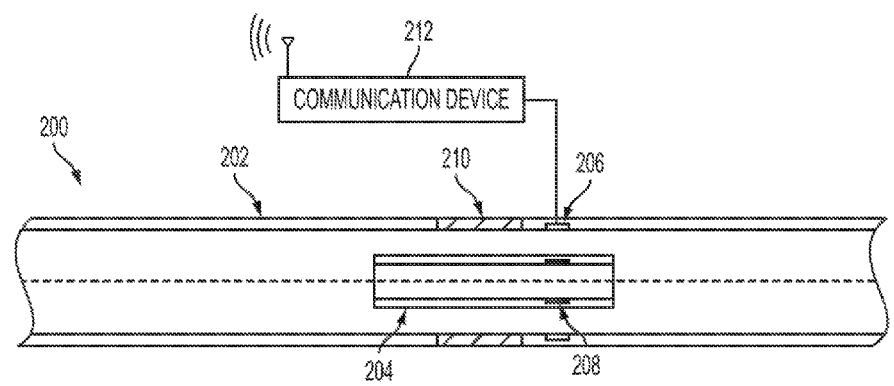
FIG. 2A is a cross-sectional side view of one embodiment of an assembly for determining bend measurements of an adjustable motor assembly using magnetometers.

FIG. 2A is a cross-sectional side view of one embodiment of an assembly for determining bend measurements of an adjustable motor assembly 200 using magnetometers. The adjustable motor assembly 200 can include a housing 202 that can bend via an adjustable ring 210. The adjustable motor assembly 200 can include a mandrel 204 inside the housing 202. The adjustable motor assembly 200 can further include a magnet 208 positioned on the mandrel such that the magnetic field emitted by the magnet 208 can be detected by a sensor 206. The sensor 206 can be positioned on a housing 202 so that the sensor 206 can detect the magnetic field emitted by the magnet 208. As the housing 202 bends, the distance between the magnet 208 and the sensor 206 can change. As the distance changes, the strength of the magnetic field measured by the sensor 206 can change. The change in the magnetic field measured by sensor 206 can be used to determine an amount of bend or bend direction of the adjustable motor assembly 200.

In other embodiments, the magnet 208 can be positioned on a rotating shaft, rather than mandrel 204, such that the magnetic field emitted by the magnet 208 can be detected by the sensor 206. The rotating shaft can rotate around a rotational axis. A change in the magnetic field detected by the sensor 206 can indicate an amount of rotation by the rotating shaft.

The sensor 206 is a magnetometer. A magnetometer according to some embodiments can measure the total strength of the magnetic field to which the magnetometer is subjected, but not the direction of the magnetic field. Examples of this type of magnetometer include a proton procession magnetometer, an Overhauser effect magnetometer, and a caesium vapor magnetometer. A magnetometer according to other embodiments can measure both the total strength of the magnetic field and the direction of the magnetic field relative to the spatial orientation of the magnetometer. Examples of this type of magnetometer include a Hall effect sensor, a magnetoresistive device, a fluxgate magnetometer, a superconducting quantum interference device, and a spin-exchange relaxation-free atomic magnetometer. In some embodiments, the sensor 206 can include a communication device 212 for communicating with a computing device, e.g. the computing device 116 depicted in FIG. 1.

Figure 2B:
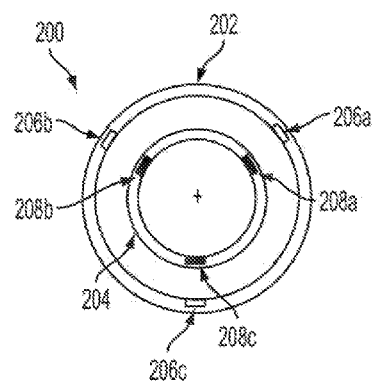
FIG. 2B is a cross-sectional end view of the embodiment in FIG. 2A in which there is no bend in the adjustable motor assembly according to one example.

In some embodiments, multiple sensors and multiple magnets can be used in the configuration shown in FIG. 2A. For example, as shown in FIG. 2B, three magnets 208a-c and three sensors 206a-c can be equally spaced around the circumference of the mandrel 204 and the housing 202, respectively, such that each sensor 206a-c can detect a magnetic field from a particular magnet 208a-c. In other embodiments, the three magnets 208a-c can be equally spaced around the circumference of the housing 202 and the three sensors 206a-c can be equally spaced around the circumference of the mandrel 204, such that each sensor 206a-c can detect a magnetic field from a particular magnet 208a-c. Magnetic field measurements from each sensor 206a-c can be used to determine a relative bend direction and bend amount of the first motor housing assembly member to the second motor housing assembly member. When there is no bend, the distance of each magnet 208a-c to its sensor 206a-c can be roughly equal and, consequently, sensor measurements can be roughly equal.

Figure 2C:
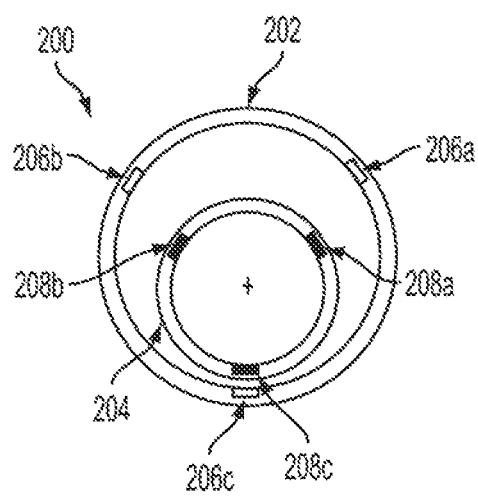
FIG. 2C is a cross-sectional end view of the embodiment in FIG. 2A in which there is a bend in the adjustable motor assembly according to one example.

FIG. 2C is a cross-sectional end view of the embodiment in FIG. 2A showing a bend in the adjustable motor assembly 200 according to one example. When there is a bend in the adjustable motor assembly 200, the distance of each magnet 208a-c to its sensor 206a-c can change. The amount of change can be based on the amount of bend or bend direction of the first motor housing assembly member relative to the second motor housing assembly member. As the distance of each magnet 208a-c to its sensor 206a-c changes, so too can the magnetic field measurements by the sensors 206a-c. The changed magnetic field measurements can be used to determine the bend direction and bend amount of the first motor housing assembly member relative to the second motor housing assembly member.

In some embodiments, the computing device 116 depicted in FIG. 1 can determine one or both of a bend direction and a bend amount based on changes in magnetic fields measured by one or more of the sensors 206a-c. For example, the computing device 116 can determine a first set of magnetic field measurements at the respective sensors 206a-c. The computing device 116 can associate the first set of magnetic field measurements with a first bend direction or bend amount (e.g., an absence of bending in any direction for an un-bent motor assembly 122), for example, associating the first set of magnetic field measurements with a first vector. Further, the computing device 116 can determine a second set of magnetic field measurements at the respective sensors 206a-c based on a bending of the motor assembly 122. The computing device 116 can associate the second set of magnetic field measurements with a second bend direction or bend amount, for example, by associating the second set of magnetic field measurements with a second vector. In some embodiments, computing device 116 can determine a change in the bend angle or direction by comparing the first vector with the second vector, for example, by comparing the direction cosines of the first and second vectors.

In other embodiments, the computing device 116 can determine a first or second bend direction or bend amount by other means. For example, an increase in the magnetic field measurement at the sensor 206a and a decrease in the magnetic field measurements at the respective sensors 206b, 206c can indicate a bend in the direction of the sensor 206a. The computing device 116 can correlate a bend amount with one or more of an amount by which the magnetic field measurement at the sensor 206a increases and the amounts by which the magnetic field measurements at the respective sensors 206b, 206c decrease.

In additional or alternative embodiments, a computing device 116 can determine an amount of rotation based on changes in magnetic fields measured by one or more of the sensors 206a-c. For example, the computing device 116 can determine a first set of magnetic field measurements at the respective sensors 206a-c. The computing device 116 can associate the first set of magnetic field measurements with a first angular orientation of a rotating shaft to which the magnets 208a-c may be attached. The computing device 116 can determine a second set of magnetic field measurements at the respective sensors 206a-c based on a rotation of the shaft. For example, an increase in the magnetic field measurement at the sensor 206a and a decrease in the magnetic field measurements at the respective sensors 206b, 206c can indicate a rotation toward the sensor 206a and away from the sensors 206b, 206c. The computing device 116 can correlate an amount of rotation with one or more of an amount by which the magnetic field measurement at the sensor 206a increases and the amounts by which the magnetic field measurements at the respective sensors 206b, 206c decrease.

Figure 3A:
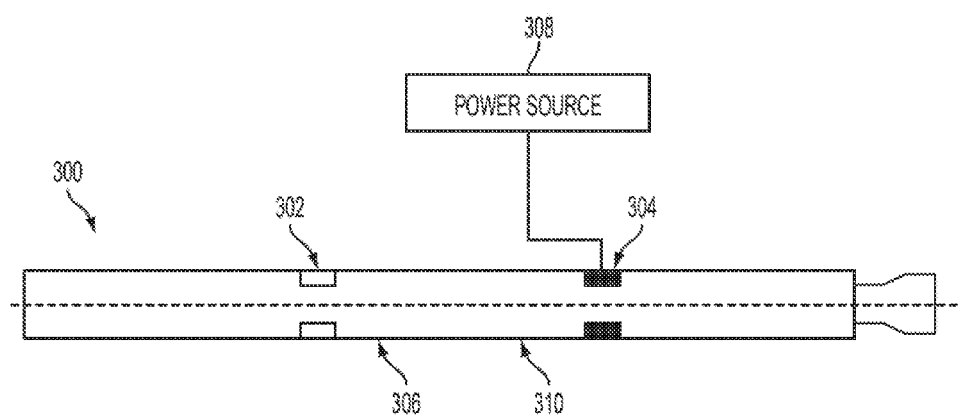
FIG. 3A is a cross-sectional side view of another embodiment of an assembly for determining bend measurements of an adjustable motor assembly using magnetometers in which there is no bend in the adjustable motor assembly according to one example.

FIG. 3A is a cross-sectional side view of another embodiment of an assembly 300 for determining bend measurements of an adjustable motor assembly 300 using magnetometers 302 in which there is no bend in the adjustable motor assembly according to one example. The adjustable motor assembly 300 can include a bendable housing 306. A sensor 302 can be positioned on a first side of a bend location 310 and a magnet 304 can be positioned on a second side of the bend location 310. In one embodiment, the magnet 304 and the sensor 302 are equidistant from the bend location 310. In another embodiment, the magnet 304 can be on the outside of the bendable housing 306 and the bendable housing 306 can be magnetically penetrable. The magnet 304 can include an electromagnet and an associated power source 308.

In some embodiments, a multitude of magnets 304 can be positioned on the first side of bend location 310 and a multitude of sensors 302 can be positioned on a second side of bend location 310. In one such embodiment, the multitude of magnets 304 can be equidistant around the circumference of the bendable housing 306 on the first side of the bend location and the multitude of sensors 302 can be equidistant around the circumference of the bendable housing 306 on the second side of the bend location.

Figure 3B:
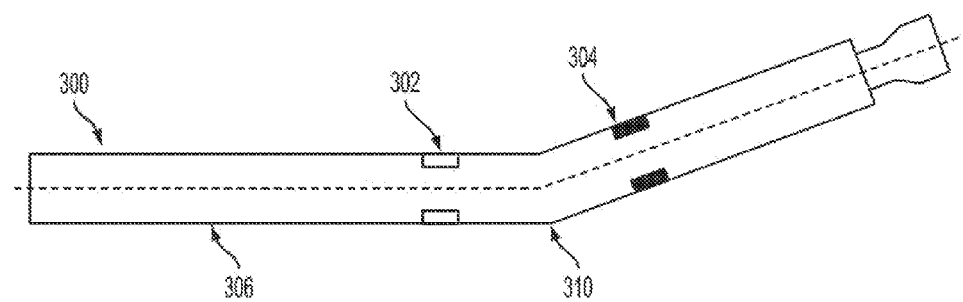
FIG. 3B is a cross-sectional side view of the embodiment in FIG. 3A in which there is a bend in the adjustable motor assembly according to one example.

When there is no bend in the housing 306, the distance of a magnet 304 to a sensor 302 can be at a maximum. If housing 306 bends, as shown in FIG. 3B, the distance between the magnet 304 and sensor 302 can decrease, causing a magnetic field strength measurement at the sensor 302 to change. The changed magnetic field strength measured by the sensor 302 can be used to determine the bend direction and bend amount in the adjustable motor assembly 300.

Figure 4A:
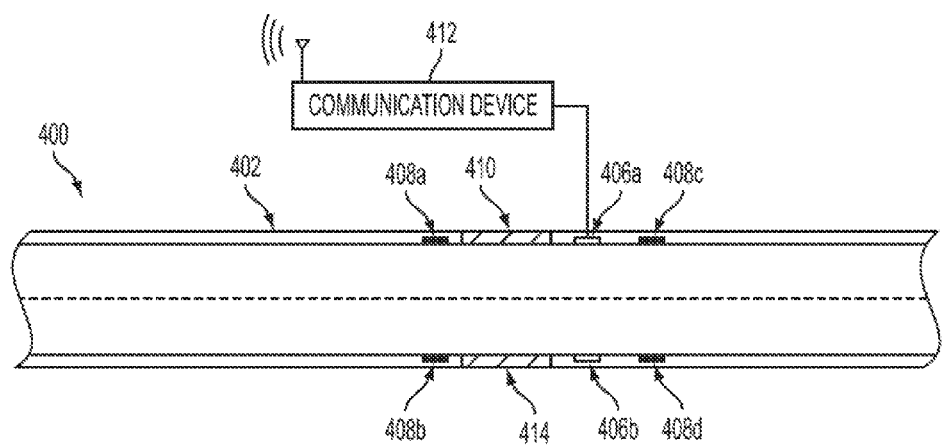
FIG. 4A is a cross-sectional side view of another embodiment of an assembly for determining bend measurements of an adjustable motor assembly using magnetometers in which there is no bend in the adjustable motor assembly according to one example.

FIG. 4A is a cross-sectional side view of another embodiment of an assembly 400 for determining bend measurements of an adjustable motor assembly 400 using magnetometers 406a, 406b. The adjustable motor assembly 400 can include a housing 402 that can bend via an adjustable ring 410. In some embodiments, the adjustable motor assembly 400 can include a mandrel inside the housing 402. The adjustable motor assembly 400 can further include a first magnet 408a positioned on the housing 402 at a first side of a bend location 414. The adjustable motor assembly 400 can further include a second magnet 408c positioned on the housing 402 at a second side of the bend location 414. A sensor 406a can be positioned on a housing 402 for detecting the combined magnetic field emitted by the magnets 408a, 408c. In some embodiments, the combined magnetic field of two cylindrical magnets can be determined by the following equation:

$$F = \left[\frac{B_0^2 A^2 (L^2 + R^2)}{\pi \mu_0 L^2}\right]\left[\frac{1}{x^2} + \frac{1}{(x+2L)^2} - \frac{2}{(x+L)^2}\right]$$

Where L is the length of the magnets, B is the magnetic flux, x is the distance between the magnets, and F is the resulting force between the two magnets. Bending the housing 402 can change the distance between the first magnet 408a and the second magnet 408c, causing the combined magnetic field between the two magnets to change. Changing the combined magnetic field can alter the strength of the magnetic field measured by the sensor 406a. The change in magnetic field measured by sensor 406a can be used to determine an amount of bend in the housing 402.

A third magnet 408b, a fourth magnet 408d, and a second sensor 406b can be positioned on the opposite side of the housing 402 from the first magnet 408a, second magnet 408c, and first sensor 406a. The third magnet 408b can be positioned on the housing 402 on a first side of a bend location 414. The fourth magnet 408d can be positioned on the housing 402 on a second side of the bend location 414. The second sensor 406b can be positioned on the housing 402 for detecting the combined magnetic field emitted by the magnets 408b, 408d. Bending the housing 402 can change the distance between the third magnet 408b and the fourth magnet 408d, altering the combined magnetic field. Altering the combined magnetic field can change the strength of the magnetic field measured by the second sensor 406b. The change in magnetic field measured by sensor 406b can be used to determine an amount of bend in the housing 402. Further, the changes in sensors 406a, 406b can be combined to determine a bend direction.

Figure 4B:
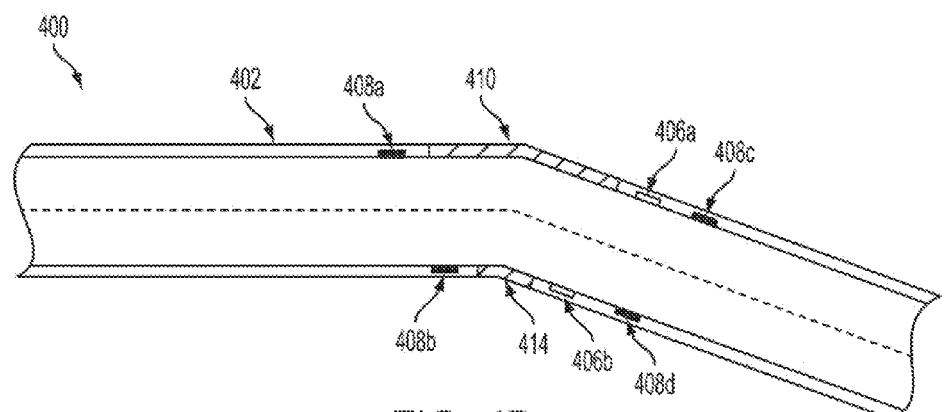
FIG. 4B is a cross-sectional side view of the embodiment in FIG. 4A in which there is a bend in the adjustable motor assembly according to one example.

For example, as depicted in FIG. 4B, bending the motor assembly 400 can increase the distance between the first magnet 408a and the second magnet 408c, and decrease the distance between the third magnet 408b and the fourth magnet 408d. The increased distance between magnet 408a and magnet 408c can cause a decrease in the combined magnetic field measured by the sensor 406a. The decreased distance between magnet 408b and magnet 408d can cause an increase in the combined magnetic field measured by the sensor 406b. The changed magnetic field measurements can be used to determine a bend amount or bend direction.

Figure 4C:
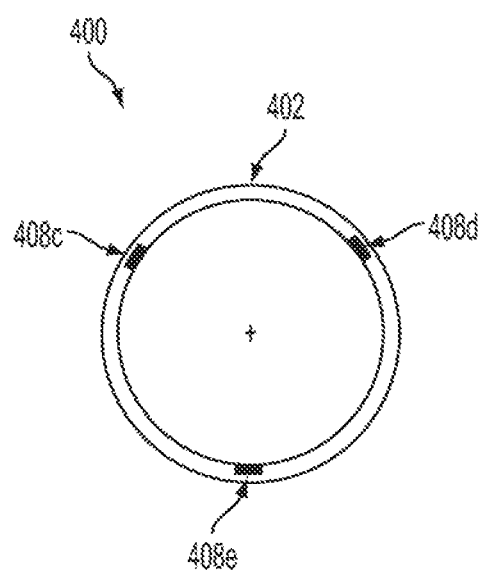
FIG. 4C is a cross-sectional end view of the embodiment in FIG. 4A in which there is no bend in the adjustable motor assembly according to one example.

FIG. 4C is a cross-sectional end view of the embodiment in FIG. 4A in which there is no bend in the adjustable motor assembly according to one example. In this example, a first set of magnets 408c-e are positioned on the housing 402 on a second side of a bend location 414. Sensors are positioned on the housing 402 behind the first set of magnets 408c-e. Further, a second set of magnets are positioned on the housing 402 and behind the sensors 406a-c on the first side of a bend location 414. When there is no bend in the adjustable motor assembly 400, the distance of each first magnet 408c-e to its associated second magnet is relatively equal. The sensors can measure the combined magnetic field emitted by each of the respective magnet pairs. A computing device, such as the computing device 116 of FIG. 1, can associate the set of magnetic field measurements with a first bend direction or bend amount, for example, by associating the magnetic field measurements with a first vector.

When there is a bend in the adjustable motor assembly 400, the distance of each first magnets 408c-e to associated second magnet can change. For example, bending the motor assembly 400 as shown in FIG. 4B can increase the distance between magnet 408c and its associated second magnet and decrease the distance between magnet 408d and its associated second magnet. The increased distance between magnet 408c and its associated magnet and can cause a decrease in the combined magnetic field measured by the sensor positioned between them. The decreased distance between magnet 408d and its associated magnet can cause an increase in the combined magnetic field measured by the sensor positioned between them. The changed magnetic field measurements can be used to determine a second vector, which can be used to determine a bend amount or bend direction. Further, in some embodiments, the second vector can be compared to the first vector to determine a change in bend amount or bend direction.

As another example, bending the motor assembly 400 horizontally to the right can increase the distance between magnet 408c and its associated magnet and decrease the distance between magnet 408d and its associated magnet. The distance between magnet 408e and its associated magnet should remain relatively the same. The changed distances can cause a change in the combined magnetic fields measured by the sensors. The changed magnetic field measurements can be used to determine a vector, which can be used to determine a bend amount or bend direction.

Figure 5:
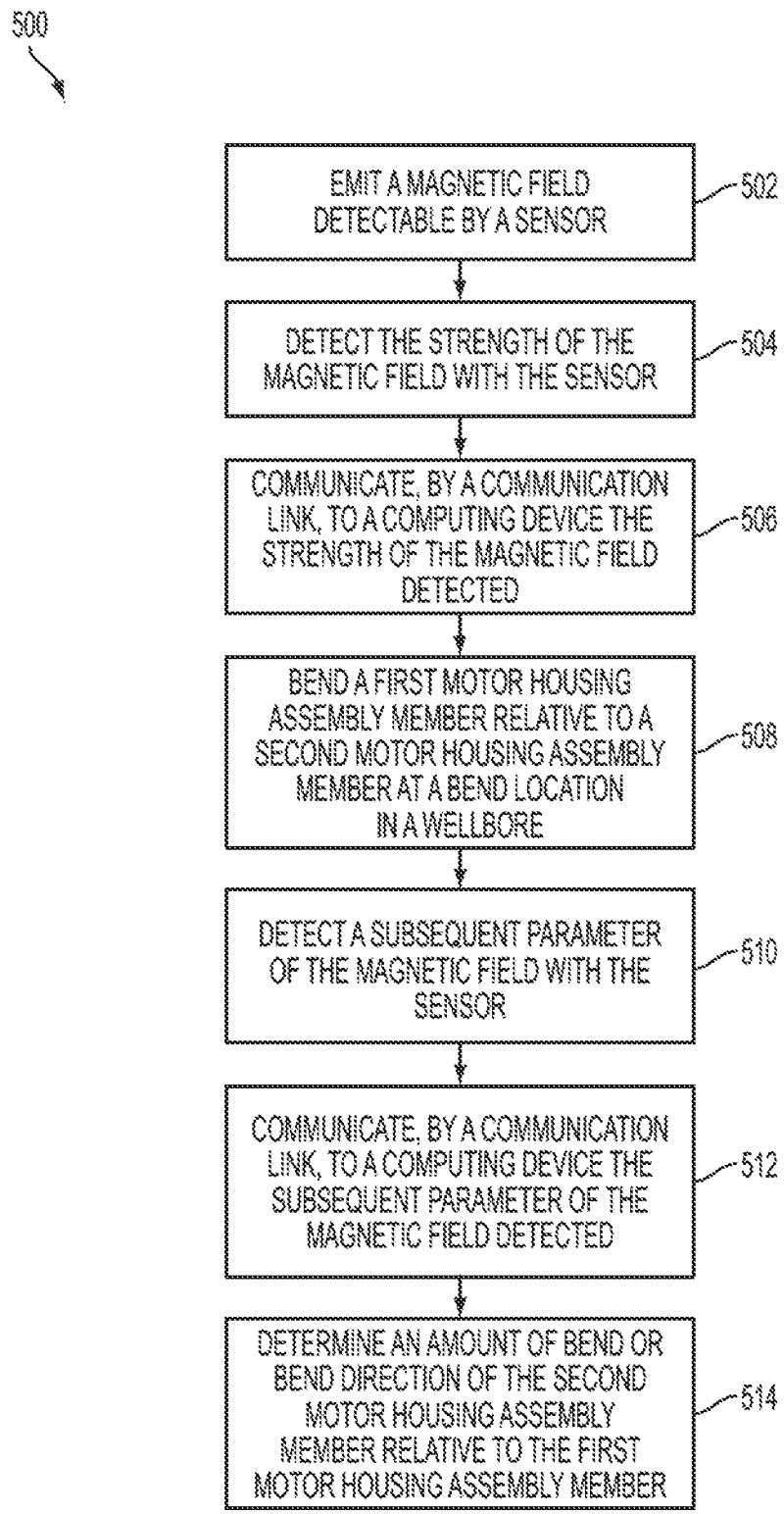
FIG. 5 is an example of a flow chart of a process for determining bend measurements of an adjustable motor assembly using magnetometers according to one embodiment.

FIG. 5 is an example of a flow chart of a process 500 for determining bend measurements of an adjustable motor assembly using magnetometers according to one embodiment.

In block 502, a magnet emits a magnetic field that can be detected by a sensor that is a magnetometer. The magnet is positioned so that the magnetic field emitted by the magnet is strong enough that it can be detected by the sensor. The magnet can be an electromagnet coupled to a power source. In one embodiment, the sensor can filter out background magnetic fields generated by sources other than the magnet. In some embodiments, the sensor can detect both the magnitude and direction of the magnetic field emitted by the magnet. Further, in some embodiments, components of the adjustable motor assembly can be magnetically penetrable.

In some embodiments, the magnet can be positioned on a first motor housing assembly member so the magnetic field emitted by the magnet can be detected by the sensor. The sensor can be positioned on a second motor housing assembly member for detecting the strength of the magnetic field emitted by the magnet. In other embodiments, the magnet can be positioned on a third motor assembly member inside the first or second motor housing assembly member, like a mandrel, so the magnetic field emitted by the magnet can be detected by the sensor. The sensor can be positioned on the first or second motor housing assembly members for detecting the strength of the magnetic field emitted by the magnet. In another embodiment, the sensor can be positioned on a third motor assembly member inside the first or second motor housing assembly member, like a mandrel, for detecting the magnetic field emitted by the magnet. The magnet can be positioned on the first or second motor housing assembly members so that the sensor can detect the strength of the magnetic field emitted by the magnet.

In block 504, the sensor detects a strength of the magnetic field emitted by the magnet. The sensor is a magnetometer. The strength of the magnetic field as detected by the sensor is a function of both the strength of the magnet and the distance between the magnet and the sensor. The detected magnetic field strength can decrease with increasing distance between the magnet and the sensor. In some embodiments, the sensor can further detect the direction of the magnetic field emitted by the magnet. The magnetic field strength detection can be used as a baseline measurement against which subsequent magnetic field detections can be compared to determine an amount of bend or bend direction of an adjustable motor assembly (such as, but not limited to, the motor assemblies 200, 300, or 400).

In block 506, the strength of the magnetic field detected is communicated, by a communication device 212, to a computing device 116. The communication can further include the direction of the magnetic field emitted by the magnet. The computing device 116 can be located at any suitable location (e.g., at the surface of the wellbore, below ground, or offsite).

In block 508, a first motor housing assembly member bends relative to a second motor housing assembly member at a bend location in a wellbore 112. In one such embodiment, a drill operator can cause the first motor housing assembly member to bend relative to the second motor housing assembly member in order to navigate around a bend in the formation of the wellbore 112. In some embodiments, the first motor housing assembly can bend relative to the second motor housing assembly member automatically in response to encountering a bend in the formation of the wellbore 112. In another embodiment, the drill operator can cause the first motor housing assembly member to bend relative to the second motor housing assembly member to drill along a designated drilling trajectory. As the first motor housing assembly member bends relative to the second motor assembly housing member, the distance between the sensor and the magnet can change. As the distance changes, the strength of the magnetic field emitted by the magnet as detected by the sensor can change.

In block 510, the sensor detects a subsequent parameter of the magnetic field. The sensor can detect a magnetic field strength or direction that has changed from the baseline magnetic field strength detection.

In block 512, the sensor communicates, by a communication device 212, to a computing device 116 the subsequent parameter of the magnetic field detected.

In block 514, the amount of bend and a bend direction of the first motor housing assembly member relative to the second motor housing assembly member is determined. In some embodiments, the bend direction and bend amount can be determined based on a comparison of the baseline magnetic field strength detected to the subsequent magnetic field parameter detected. The amount of change in the sensor measurements can be indicative of the amount of bend and bend direction of the first motor housing assembly member relative to a second motor housing assembly member. In one embodiment, the sensor can determine the amount of bend and a bend direction of the first motor housing assembly member relative to the second motor housing assembly member. In other embodiments, the computing device 116 can determine the amount of bend and a bend direction of the first motor housing assembly member relative to the second motor housing assembly member.

In some embodiments, the computing device 116 can receive the amount of bend and bend direction via a communication device 212 and compare it with a designated drilling trajectory. Should the amount of bend and bend direction received by the computing device 116 need to be altered to conform with the designated drilling trajectory, the computing device 116 can cause the amount of bend or bend direction of the second motor housing assembly member relative to the first motor housing assembly member to change.

Figure 6:
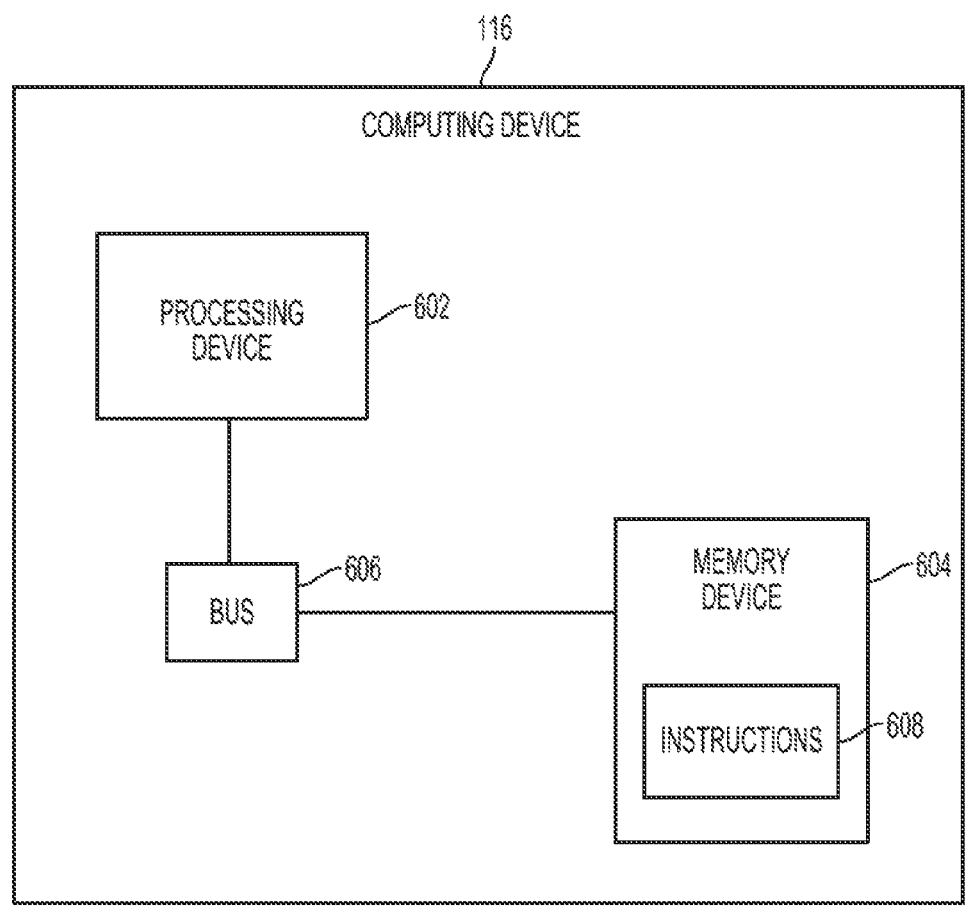
FIG. 6 is a block diagram depicting an example of a computing device for determining bend measurements of an adjustable motor assembly using magnetometers.

FIG. 6 is a block diagram depicting an example of a computing device 116 for determining bend measurements of an adjustable motor assembly using magnetometers. The computing device 116 includes a processing device 602, a memory device 604, and a bus 606.

The processing device 602 can execute one or more operations determining bend measurements of an adjustable motor assembly using magnetometers. The processing device 602 can execute instructions 608 stored in the memory device 604 to perform the operations. The processing device 602 can include one processing device or multiple processing devices. Non-limiting examples of the processing device 602 include a Field-Programmable Gate Array ("FPGA"), an application-specific integrated circuit ("ASIC"), a microprocessor, etc.

The processing device 602 can be communicatively coupled to the memory device 604 via the bus 606. The non-volatile memory device 604 may include any type of memory device that retains stored information when powered off. Non-limiting examples of the memory device 604 include electrically erasable programmable read-only memory ("ROM"), flash memory, or any other type of non-volatile memory. In some aspects, at least some of the memory device 604 can include a medium from which the processing device 602 can read instructions. A computer-readable medium can include electronic, optical, magnetic, or other storage devices capable of providing the processing device 602 with computer-readable instructions or other program code. Non-limiting examples of a computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, etc.

In some aspects, an assembly for determining bend measurements of an adjustable motor assembly using magnetometers is provided according to one or more of the following examples.

Example #1: An assembly for determining bend measurements of an adjustable motor assembly using magnetometers can include a first motor housing assembly member. The assembly can also include a second motor housing assembly member, a magnet, and a sensor. The second motor housing assembly member can be coupled to the first motor housing assembly member and bendable relative to the first motor housing assembly member at a bend location in a wellbore. The magnet can be positioned such that the sensor can detect the strength of the magnetic field emitted by the magnet. The sensor can be magnetically coupleable with the magnet and positioned to determine an amount of bend of the second motor housing assembly member relative to the first motor housing assembly member by detecting a strength of the magnetic field emitted by the magnet.

Example #2: The assembly of Example #1 may feature magnetometers further positioned to determine a bend direction.

Example #3: The assembly of any of Examples #1-2 may feature a communication device communicatively coupled with a computing device.

Example #4: The assembly of any of Examples #1-3 may feature the first motor assembly housing member or the second motor assembly housing member including a motor operatively coupleable to a drill bit.

Example #5: The assembly of any of Examples #1-4 may feature a magnet positioned on a first side of the bend location and the sensor positioned on a second side of the bend location.

Example #6: The assembly of any of Examples #1-5 may feature the magnet positioned on the exterior of the first motor assembly housing member.

Example #7: The assembly of any of Examples #1-6 may feature the first motor assembly housing member being magnetically penetrable.

Example #8: The assembly of any of Examples #1-7 may feature the sensor positioned on the exterior of the second motor assembly housing member.

Example #9: The assembly of any of Examples #1-8 may feature the magnet and the sensor located equidistant from the bend location.

Example #10: The assembly of any of Examples #1-9 may feature the magnet being included in a multitude of magnets that are positioned on the first side of the bend location.

Example #11: The assembly of Example #10 may feature the multitude of magnets equidistantly spaced around the circumference of the first motor housing assembly member.

Example #12: The assembly of any of Examples #10-11 may feature a sensor being included in a multitude of sensors that are positioned on the second side of the bend location and magnetically coupleable with the multitude of magnets.

Example #13: The assembly of Example #12 may feature the multitude of sensors equidistantly spaced around the circumference of the second motor housing assembly member.

Example #14: The assembly of any of Examples #1-5, 7, 9-10, and 12 may feature a third motor assembly member inside the first motor housing assembly member or the second motor housing assembly member.

Example #15: The assembly of Example #14 may feature the magnet positioned on the third motor assembly member.

Example #16: The assembly of Example #15 may feature the magnet being included in a multitude of magnets that are positioned on the third motor assembly member.

Example #17: The assembly of Example #16 may feature the multitude of magnets equidistantly spaced around the circumference of the third motor assembly member.

Example #18: The assembly of any of Examples #14-17 may feature the third motor assembly member being rotatable around a rotation axis.

Example #19: A method for determining bend measurements of an adjustable motor assembly using magnetometers can include emitting a magnetic field from a magnet. The sensor can detect the strength of the magnetic field. The sensor can communicate, by a communication device, to a computing device the strength of the magnetic field detected. A first motor housing assembly member can bend relative to a second motor housing assembly member at a bend location in a wellbore. The sensor can detect a subsequent parameter of the magnetic field emitted by the magnet. The sensor can communicate, by a communication device, to a computing device the subsequent parameter of the magnetic field detected. Finally, the assembly can determine an amount of bend or bend direction of the second motor housing assembly member relative to the first motor housing assembly member based on the strength of the magnetic field emitted by the magnet.

Example #20: The method of Example #19 may feature determining an amount of bend second motor housing assembly member relative to the first motor housing assembly member by associating the strength of the magnetic field detected by the sensor with a first bend amount. The computing device can associate the subsequent parameter of the magnetic field detected by the sensor with a second bend amount. Further, the computing device can determine the difference between the first bend amount and the second bend amount.

Example #21: The method of any of Examples #19-20 may feature determining a bend direction of the second motor housing assembly member relative to the first motor housing assembly member by associating the strength of the magnetic field detected by the sensor with a first bend direction. The computing device can associate the subsequent parameter of the magnetic field detected by the sensor with a second bend direction. Finally, the computing device can determine the difference between the first bend direction and the second bend direction.

Example #22: The method of any of Examples #19-21 may feature determining if the bend direction and bend amount should be altered to conform with a designated drilling trajectory. Further, the method may feature causing the amount of bend or bend direction of the second motor housing assembly member relative to the first motor housing assembly member to change.

Example #23: A computing device for determining bend measurements of an adjustable motor assembly using magnetometers can include a processing device and a memory. The memory can include instructions executable by the processing device. The instructions can include receiving a strength of a magnetic field detected by a sensor, and receiving a subsequent parameter of the magnetic field detected by the sensor. Further, the instructions can include determining an amount of bend or bend direction of a second motor housing assembly member relative to a first motor housing assembly member based on the strength of the magnetic field detected by the sensor.

Example #24: The computing device of Example #23 may feature instructions for associating the strength of the magnetic field detected by the sensor with a first bend amount and associating the subsequent parameter of the magnetic field detected by the sensor with a second bend amount. The computing device may further feature instructions for determining the difference between the first bend amount and the second bend amount.

Example #25: The computing device of any of Examples #23-24 may feature instructions for associating the strength of the magnetic field detected by the sensor with a first bend direction. The computing device may feature instructions for associating the subsequent parameter of the magnetic field detected by the sensor with a second bend direction. Finally, the computing device may feature instructions for determining the difference between the first bend direction and the second bend direction.

Example #26: The computing device of any of Examples #23-25 may feature instructions for determining if the amount of bend or bend direction should be altered to conform with a designated drilling trajectory and causing the amount of bend or bend direction of the second motor housing assembly member relative to the first motor housing assembly member to change.

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. An assembly usable with a drill string in a wellbore, the assembly comprising:
   a first motor assembly housing member comprising a magnet;
   a second motor assembly housing member coupled to the first motor housing assembly member and bendable relative to the first motor housing assembly member at a bend location in the wellbore, the second motor assembly housing member comprising a sensor that is magnetically coupleable with the magnet for detecting a strength of a magnetic field emitted by the magnet; and
   an adjustable ring positioned between the magnet and the sensor, the adjustable ring being a selectively bendable joint for angling the first motor assembly housing member relative to the second motor assembly housing member.

2. The assembly of claim 1, wherein the sensor is further positioned to determine a bend direction.

3. The assembly of claim 1, further comprising a communication device communicatively coupled with a computing device.

4. The assembly of claim 1, wherein the first motor assembly housing member or the second motor assembly housing member comprises a motor operatively coupleable to a drill bit.

5. The assembly of claim 1, wherein the magnet is positioned on a first side of the bend location and the sensor is positioned on a second side of the bend location.

6. The assembly of claim 5, wherein the magnet is positioned on an exterior of the first motor assembly housing member.

7. The assembly of claim 6, wherein the first motor assembly housing member is magnetically penetrable.

8. The assembly of claim 5, wherein the sensor is positioned on an exterior of the second motor assembly housing member.

9. The assembly of claim 5, wherein the magnet and the sensor are equidistant from the bend location.

10. The assembly of claim 5, wherein the magnet is a plurality of magnets that are positioned on the first side of the bend location.

11. The assembly of claim 10, wherein the plurality of magnets are equidistant around a circumference of the first motor housing assembly member.

12. The assembly of claim 10, wherein the sensor is a plurality of sensors that are positioned on the second side of the bend location and magnetically coupleable with the plurality of magnets.

13. The assembly of claim 12, wherein the plurality of sensors are equidistant around a circumference of the second motor housing assembly member.

14. The assembly of claim 1, further comprising a third motor assembly member inside the first motor housing assembly member.

15. The assembly of claim 14, wherein the magnet is positioned on the third motor assembly member.

16. The assembly of claim 15, wherein the magnet is a plurality of magnets that are positioned on the third motor assembly member.

17. The assembly of claim 16, wherein the plurality of magnets are equidistant around a circumference of the third motor assembly member.

18. The assembly of claim 14, wherein the third motor assembly member is rotatable around a rotation axis.

19. A method, comprising:
emitting a magnetic field via a magnet that is included in a first motor housing assembly member;
detecting a strength of the magnetic field with a sensor that is included in a second motor housing assembly member, wherein an adjustable ring is positioned between the magnet and the sensor, the adjustable ring being a selectively bendable joint for angling the first motor assembly housing member relative to the second motor assembly housing member;
communicating, by a communication device, the strength of the magnetic field detected by the sensor to a computing device;
bending the first motor housing assembly member relative to the second motor housing assembly member at a bend location in a wellbore;
after bending the first motor housing assembly member relative to the second motor housing assembly member, detecting another strength of the magnetic field with the sensor;
communicating, by the communication device, the other strength of the magnetic field to the computing device; and
determining an amount of bend or a bend direction of the second motor housing assembly member relative to the first motor housing assembly member based on (i) the strength of the magnetic field detected by the sensor and (ii) the other strength of the magnetic field detected by the sensor.

20. The method of claim 19, wherein determining the amount of bend in the second motor housing assembly member relative to the first motor housing assembly member comprises:
associating the strength of the magnetic field detected by the sensor with a first bend amount;
associating the other strength of the magnetic field detected by the sensor with a second bend amount; and
determining a difference between the first bend amount and the second bend amount.

21. The method of claim 19, wherein determining the bend direction of the second motor housing assembly member relative to the first motor housing assembly member comprises:
associating the strength of the magnetic field detected by the sensor with a first bend direction;
associating the other strength of the magnetic field detected by the sensor with a second bend direction; and
determining a difference between the first bend direction and the second bend direction.

22. The method of claim 19, further comprising:
determining if the bend direction or the amount of bend should be altered to conform with a designated drilling trajectory; and
causing the amount of bend or the bend direction of the second motor housing assembly member relative to the first motor housing assembly member to change.

23. A computing device comprising:
a processing device; and
a memory device comprising instructions executable by the processing device for causing the processing device to:
receive, from a sensor positioned on a second motor assembly housing member, a first strength of a magnetic field emitted by a magnet that is positioned on a first motor assembly housing member;
receive, from the sensor, a second strength of the magnetic field emitted by the magnet; and
determine an amount of bend or a bend direction of the second motor housing assembly member relative to the first motor housing assembly member by comparing (i) the first strength of the magnetic field to (ii) the second strength of the magnetic field.

24. The computing device of claim 23, wherein the memory device further comprises instructions that are executable by the processing device for causing the processing device to:
associate the first strength of the magnetic field detected by the sensor with a first bend amount;
associate the second strength of the magnetic field detected by the sensor with a second bend amount; and
determine a difference between the first bend amount and the second bend amount.

25. The computing device of claim 23, wherein the memory device further comprises instructions that are executable by the processing device for causing the processing device to:
associate the first strength of the magnetic field detected by the sensor with a first bend direction;
associate the second strength of the magnetic field detected by the sensor with a second bend direction; and
determining a difference between the first bend direction and the second bend direction.

26. The computing device of claim 23, wherein the instructions executable by the processing device further comprise instructions for:
  determining if the bend direction or the amount of bend should be altered to conform with a designated drilling trajectory; and
  causing the amount of bend or the bend direction of the second motor housing assembly member relative to the first motor housing assembly member to change.

\* \* \* \* \*